United States Patent [19]

Aebi et al.

[11] Patent Number: 5,574,071
[45] Date of Patent: Nov. 12, 1996

[54] METHOD OF LOWERING CHOLESTEROL

[75] Inventors: Johannes Aebi; Philipe Guerry, both of Basel; Synése Jolidon, Birsfelden, all of Switzerland; Olivier Morand, Hegenheim, France

[73] Assignee: Hoffmann-La Roche Inc., Nutley, N.J.

[21] Appl. No.: 468,114

[22] Filed: Jun. 6, 1995

Related U.S. Application Data

[62] Division of Ser. No. 261,615, Jun. 17, 1994, Pat. No. 5,495,048.

[30] Foreign Application Priority Data

Jul. 14, 1993 [CH] Switzerland .............................. 2107/93
Apr. 28, 1994 [CH] Switzerland .............................. 1320/94

[51] Int. Cl.$^6$ .................................................. A61K 31/135
[52] U.S. Cl. ........................ 514/648; 514/524; 514/650; 514/651; 514/654
[58] Field of Search ............................... 514/524, 648, 514/650, 651, 654

[56] References Cited

U.S. PATENT DOCUMENTS

| | | | |
|---|---|---|---|
| 3,647,863 | 3/1972 | Palopoli et al. | 562/584 |
| 3,928,449 | 12/1975 | Griot | 564/339 |
| 5,106,878 | 4/1992 | Guerry et al. | 514/651 |
| 5,137,920 | 8/1992 | Guerry et al. | 514/648 |
| 5,177,067 | 1/1993 | Guerry et al. | 514/183 |
| 5,214,046 | 5/1993 | Guerry et al. | 514/255 |
| 5,239,084 | 8/1993 | Guerry et al. | 548/578 |

OTHER PUBLICATIONS

M. Krieger, Anal. Biochem. 135, pp. 383–391 (1983).
D. L. Brasaemle & Attie A. D., Biotechniques 6, pp. 418–419 (1988).
J. Biol. Chem. 256, pp. 11923–11931 (1981).
Gebre–Hiwot, et al., J. of Antimicrobial Chemotherapy, 32:837–842 (1993) "The In–vitro Anti–leishmanial Activity of Inhibitors . . . ".
Jolidon, et al., Proceed. of the Third International Symposium on Molecular Aspects of Chemotherapy, Jun. 19–21, 1991, Gdansk, Poland, pp. 143–152.
Gerst, et al., Biochem. Pharmacology 37(10):1955–1964 (1988) "Potent Inhibition of Cholesterol Biosynthesis in 3T3 Fibroblasts".
Boissier et al., Chemical Abstracts, vol. 68, abstract 39231e. 1968.

*Primary Examiner*—Richard L. Raymond
*Attorney, Agent, or Firm*—George W. Johnston; Raina Semionow

[57] ABSTRACT

A method of lowering cholesterol which comprises administering to a host requiring such treatment an effective amount of a compound of the formula

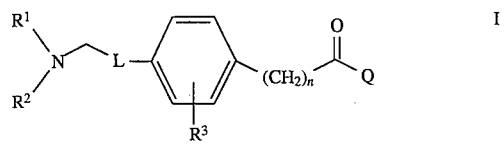

wherein
one of $R^1$ and $R^2$ is $C_{1-7}$-alkyl and the other is $C_{1-7}$-alkyl or $C_{2-6}$-alkenyl-methyl;
L is $C_{1-11}$-alkylene or $C_{2-11}$-alkenylene optionally bonded to the phenyl group via an O atom or L is 1,4-phenylene;
n is 0 or, when L contains an O atom, n is 0 or 1;
Q is $C_{1-7}$-alkyl, $C_{2-10}$alkenyl or a group of formula

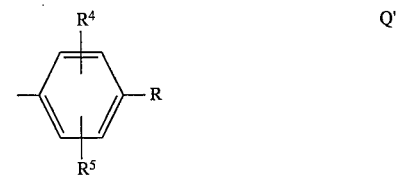

wherein R is H, halogen, $CF_3$, CN or $NO_2$;
$R^3$ and $R^4$ are H, $C_{1-4}$-alkyl or halogen; and
$R^5$ is H or, when R is H, $R^5$ is H or halogen;
or a pharmaceutically acceptable acid addition salt thereof, as well as certain compounds of formula I, are described.

14 Claims, No Drawings

METHOD OF LOWERING CHOLESTEROL

This is a division, of application Ser. No. 08/261,615 filed Jun. 17, 1994, now U.S. Pat. No. 5,495,048.

BRIEF SUMMARY OF THE INVENTION

The invention relates to a method of lowering cholesterol which comprises administering to a host requiring such treatment an effective amount of a compound of the formula

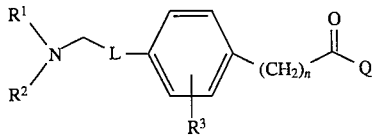

wherein
one of $R^1$ and $R^2$ is $C_{1-7}$-alkyl and the other is $C_{1-7}$-alkyl or $C_{2-6}$-alkenyl-methyl;

L is $C_{1-11}$-alkylene or $C_{2-11}$-alkenylene optionally bonded to the phenyl group via an O atom or L is 1,4-phenylene;

n is 0 or, when L contains an O atom, n is 0 or 1;

Q is $C_{1-7}$-alkyl, $C_{2-10}$-alkenyl or a group of formula

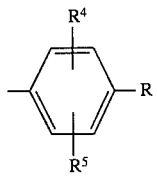

wherein R is H, halogen, $CF_3$, CN or $NO_2$; $R^3$ and $R^4$ are H, $C_{1-4}$alkyl or halogen; and $R^5$ is H or, when R is H, $R^5$ is H or halogen;

or a pharmaceutically acceptable acid addition salt thereof.

DETAILED DESCRIPTION OF THE INVENTION

The invention relates to a method of lowering cholesterol which comprises administering to a host requiring such treatment an effective amount of a compound of the formula

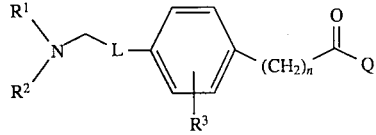

wherein
one of $R^1$ and $R^2$ is $C_{1-7}$-alkyl and the other is $C_{1-7}$-alkyl or $C_{2-6}$-alkenyl-methyl;

L is $C_{1-11}$-alkylene or $C_{2-11}$-alkenylene optionally bonded to the phenyl group via an O atom or L is 1,4-phenylene;

n is 0 or, when L contains an O atom, n is 0 or 1;

Q is $C_{1-7}$-alkyl, $C_{2-10}$-alkenyl or a group of formula

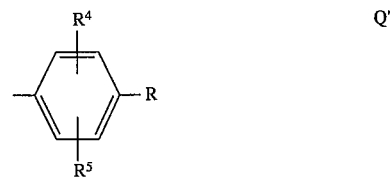

wherein R is H, halogen, $CF_3$, CN or $NO_2$;
$R^3$ and $R^4$ are H, $C_{1-4}$-alkyl or halogen; and
$R^5$ is H or, when R is H, $R^5$ is H or halogen;

or a pharmaceutically acceptable acid addition salt thereof.

In a further aspect, the invention relates to species which fall under formula I, such as the following:

4-[[6-( Allylmethylamino)hexyl]oxy]-3-chlorobenzophenone;

4-[[6-(allylmethylamino)hexyl]oxy]-3,4'-dibromobenzo phenone;

4-[[4-(allymethylamino)-2-butenyl]oxy]-3,4'-dibromobenzophenone;

3-chloro-4'-iodo-4-[[6-(allymethylamino)hexyl]oxy]benzophenone;

4'-bromo-3-chloro-4-[[6-(allymethylamino)hexyl]oxy] benzophenone;

2,4-[[(4-dimethylamino)-2-butenyl]oxy]-3,4'-dibromobenzophenone;

4-[[4-(dimethylamino)-2-butenyl]oxy]-3-chlorobenzophenone;

4'-bromo-3-chloro-4-[[6-(dimethylamino)hexyl]oxy]benzophenone;

3,4-dichlorophenyl 4'-[(dimethylamino)methyl]-4-biphenylyl ketone;

4'-[(allylmethylamino)methyl]-4-biphenylyl 3,4-dichlorophenyl ketone;

(RS)-4'-(dimethylaminomethyl)-4-biphenyl 2,6-dimethyl-5-heptenyl ketone;

p-bromophenyl 2-chloro-4'-[(dimethylamino)methyl]-4-biphenylyl ketone;

4'-[(dimethylamino)methyl]-4-biphenylyl propyl ketone;

[4-[6-(ally-methyl-amino)-hexyloxy]-phenyl]-(4-bromo-phenyl)-methanone;

[4-[4-(ally-methyl-amino)-butoxy]-phenyl]-(4-bromo-phenyl)-methanone;

[4-[6-(ally-methyl-amino)-hexyloxy]-3-fluoro-phenyl]-(4-bromo-phenyl)-methanone;

[4-[6-(ally-methyl-amino)-hexyloxy]-2-fluoro-phenyl]-(4-bromo-phenyl)-methanone;

(E)-[4-[4-(ally-methyl-amino)-but-2-enyloxy]-phenyl]-(4-trifluoromethyl-phenyl)-methanone;

(E)-[4-[4-(ally-methyl-amino)-but-2-enyloxy]-3-fluoro-phenyl]-(4-bromo-phenyl)-methanone;

(E)-1-[4-[4-(ally-methyl-amino)-but-2-enyloxy]-phenyl]-5-methyl-hexan-1-one;

( E)-[4-[4-(ally-methyl-amino)-but-2-enyloxy]-phenyl]-(4-iodo-phenyl)-methanone;

(E)-1-[4-(ally-methyl-amino)-but-2-enyloxy]-3-fluoro-phenyl]-5-methyl-hexan-1-one;

(E)-[4-[4-(ally-methyl-amino)-but-2-enyloxy]-3-fluoro-benzoyl]-benzonitrile;

(E)-4-[4-[4-(allyl-methyl-amino)-but-2-enyloxy]-benzoyl]-benzonitrile;

(E)-[4-[4-(ally-methyl-amino)-but-2-enyloxy]-3-fluoro-phenyl]-(2,6-difluoro-phenyl)-methanone;

(E)-1-[4-[4-(ally-methyl-amino)-but-2-enyloxy]-phenyl]-5-methyl-hex-4-en-1-one;

(E)-[4-[4-(ally-methyl-amino)-but-2-enyloxy]-2-fluoro-phenyl]-(4-bromo-phenyl)-methanone;

(E)-[4-[4-(ally-methyl-amino)-but-2-enyloxy]-phenyl]-(4-fluoro-phenyl)-methanone;

(E)-1-[4-[4-(ally-methyl-amino)-but-2-enyloxy]-3-fluoro-phenyl]-6-methyl-hept-5-en-2-one;

(E)-2-[4-[4-(allyl-methyl-amino)-but-2-enyloxy]-3-fluoro-phenyl]-1-(4-bromo-phenyl)-ethanone;

(E)-2-[4-[4-(allyl-methyl-amino)-but-2-enyloxy)-phenyl]-1-(4-bromo-phenyl)-ethanone;

(E)-(4-bromo-phenyl)-[4-[4-(ethyl-methyl-amino)-but-2-enyloxy]-phenyl]-methanone;

4'-[(allylmethylamino)methyl]-2-chloro-4-biphenylyl p-bromophenyl ketone; and

4'-[(allylmethylamino)methyl]-4-biphenyl 4-methyl-3-pentenyl ketone.

As used herein, the terms "alkyl" and "alkylene" denote straight-chain or branched, saturated hydrocarbon residues having one or two, respectively, valencies, such as, methyl, ethyl, propyl, isobutyl, t-butyl and the like and, respectively, methylene, pentamethylene, hexamethylene and the like. The terms "alkenyl" and "alkenylene" denote straight-chain or branched hydrocarbons which contain a double bond and which have one or two respectively, free valencies, such as, vinyl, propenyl and the like, and respectively, propenylene and the like.

Salts of the compounds I with inorganic and organic acids, such as, HCl, HBr, $H_2SO_4$, $HNO_3$, citric acid, acetic acid, succinic acid, fumaric acid, tartaric acid, methanesulfonic acid and p-toluenesulfonic acid, as pharmaceutically acceptable acid addition salts, also form part of the invention, and can be prepared according to known processes. Preferred compounds or formula I are those wherein n is 0 and $R^5$ is H.

Other preferred compounds of formula I are those wherein:
a) $R^1$ is methyl and $R^2$ is methyl, ethyl, propyl or allyl; and/or
b) L is the group —CH=CHCH$_2$O—, especially in the trans form, —(CH$_2$)$_5$—, —(CH$_2$)$_6$—, —(CH$_2$)$_3$O—, —(CH$_2$)$_5$O—, —(CH$_2$)$_6$O— or 1,4-phenylene; and/or
c) $R^3$ is H, Br, Cl, F or CH$_3$; and/or
d) Q is propyl, pentyl, isohexyl, 4-methyl-3-pentenyl or 2,6-dimethyl-5-heptenyl; or
e) Q is a group Q' in which R is H, Br, Cl, F, I, CF$_3$, CN or NO$_2$, and/or $R^4$ is H, Br, Cl, F or CH$_3$, and/or $R^5$ is H or F.

Especially preferred are compounds of formula I, wherein;
a) L is $C_{5-11}$-alkylene or $C_{5-11}$-alkyleneoxy, especially -(CH$_2$)$_6$- or —(CH$_2$)$_5$O—; $C_{3-11}$-alkenyloxy, especially —CH=CHCH$_2$O—, or 1,4-phenylene; and/or
b) $R^3$ is H or halogen; and/or
c) Q is $C_{2-10}$-alkenyl, especially 4-methyl-3-pentenyl; or a group Q' in which R is CN, NO$_2$ or halogen, especially Br, Cl or F, and $R^4$ is H or Cl, and, particularly those in which;
a) $R^1$ is methyl and $R^2$ is methyl or allyl; and/or
b) L is-(CH$_2$)$_5$O—, —CH=CHCH$_2$O—or 1,4-phenylene; and/or
c) $R^3$ is H or F; and/or
d) Q is 4-methyl-3-pentenyl or a group Q' in which R is Br, Cl, CN or NO$_2$, $R^4$ is H or Cl and $R^5$ is H.

Examples of preferred compounds of formula I are trans-4-[[4-(allymethylamino)-2-butenyl]oxy]-4'-bromo-benzophenone;

trans-4-[[4-(allylmethylamino)-2-butenyl]oxy]-4'-nitro-benzophenone;

p-[[4'-[(allylmethylamino)methyl]-4-biphenylyl]carbonyl]-benzonitrile;

2-chloro-4-nitrophenyl 4'-[(dimethylamino)methyl]-4-biphenylyl ketone;

trans-4-[[4-(allymethylamino)-2-butenyl]oxy]-2',4'-dichloro-benzophenone;

[4-[6-(ally-methyl-amino)-hexyloxy]-phenyl]-(4-bromo-phenyl)-methanone;

[4-[6-(ally-methyl-amino)-hexyloxy]-3-fluoro-phenyl]-(4-bromo-phenyl)-methanone;

[4-[6-(allyl-methyl-amino)-hexyloxy]-2-fluoro-phenyl]-(4-bromo-phenyl)-methanone;

(E)-[4-[4-(ally-methyl-amino)-but-2-enyloxy]-3-fluoro-phenyl]-(4-bromo-phenyl)-methanone;

(E)-1-[4-[4-(ally-methyl-amino)-but-2-enyloxy]-phenyl]-5-methyl-hex-4-en-1-one; and (E)-[4-[4-(ally-methyl-amino)-but-2-enyloxy]-2-fluoro-phenyl]-(4-bromo-phenyl)-methanone.

The compounds of formula I and their salts can be prepared as described in US Pat. Nos. 5,106,878, 5,137,920 and 5,177,067. Those compounds which are not specifically named in these patents are also an object of the invention. The preparation of such compounds is described in the Examples which follow.

The compounds I and their salts have cholesterol-lowering activity and can, accordingly, be used, especially in the control or prevention of hypercholesterolemia and atherosclerosis which are responsible for the majority of cardiovascular diseases.

The experiment described by M. Krieger (Anal. Biochem. 135, 1983, 383–391), as modified by D. L. Brasaemle and Attie A. D. (Biotechniques 6, 1988, 418–419), was carried out to demonstrate the cholesterol-lowering activity of the compounds of formula I and their salts. The property of a cholesterol synthesis inhibitor to protect CHO-K1 cells (ovarian cells from the Chinese hamster) against the cytotoxic effects of the polyene antibiotic amphotericin B is used in this experiment. The inhibition of the cholesterol synthesis is expressed as a protection of the living cells and this protection is, moreover, expressed as the number of surviving cells in comparison to untreated cells. The $EC_{50}$ value in nM/l in the Table that follows is the concentration at which 50% of the cells survive.

TABLE A

| Compound No. | $R^2$ | L | $R^3$ | Q | $EC_{50}$ nM/l |
|---|---|---|---|---|---|
| 1 | Allyl | CH=CHCH$_2$O | H | 4-Bromophonyl | 0.015 |
| 2 | Allyl | 1,4-C$_6$H$_4$ | H | 4-Cyanophenyl | 0.015 |
| 3 | Allyl | CH=CHCH$_2$O | H | 4-Nitrophenyl | 0.032 |
| 4 | CH$_3$ | 1,4-C$_6$H$_4$ | H | 2-Chloro-4-nitrophenyl | 0.046 |
| 5 | CH$_3$ | 1,4-C$_6$H$_4$ | H | 4-Nitrophenyl | 0.049 |
| 6 | CH$_3$ | 1,4-C$_6$H$_4$ | H | 4-Cyanophenyl | 0.066 |
| 7 | Allyl | CH=CHCH$_2$O | H | 2,4-Dichlorophenyl | 0.077 |
| 8 | Allyl | 1,4-C$_6$H$_4$ | H | 4-Nitrophenyl | 0.078 |
| 9 | CH$_3$ | 1,4-C$_6$H$_4$ | H | 4-Bromophenyl | 0.21 |
| 10 | CH$_3$ | 1,4-C$_6$H$_4$ | H | 2-Bromo-4-chlorophenyl | 0.26 |
| 11 | CH$_3$ | CH=CHCH$_2$O | H | 2,4-Dichlorophenyl | 0.42 |
| 12 | Allyl | 1,4-C$_6$H$_4$ | H | 4-Bromophenyl | 0.43 |
| 13 | CH$_3$ | CH=CHCH$_2$O | H | 4-Bromophenyl | 0.62 |
| 14 | Allyl | 1,4-C$_6$H$_4$ | H | 2-Chloro-4-nitrophenyl | 0.66 |
| 15 | Allyl | (CH$_2$)$_5$O | H | 4-Nitrophenyl | 0.71 |
| 16 | CH$_3$ | 1,4-C$_6$H$_4$ | H | 2,4-Dibromophenyl | 0.71 |
| 17 | Allyl | 1,4-C$_6$H$_4$ | H | 4-Iodophenyl | 0.72 |
| 18 | Allyl | 1,4-C$_6$H$_4$ | H | 2-Bromo-4-chlorophenyl | 0.73 |
| 19 | Allyl | 1,4-C$_6$H$_4$ | 2-CH$_3$ | 4-Bromophenyl | 0.80 |
| 20 | CH$_3$ | 1,4-C$_6$H$_4$ | H | 4-Methyl-3-pentenyl | 0.80 |
| 21 | CH$_3$ | 1,4-C$_6$H$_4$ | H | 4-Fluorophenyl | 0.90 |
| 22 | Allyl | (CH$_2$)$_5$O | H | 2,4-Dichlorophenyl | 0.91 |
| 23 | CH$_3$ | 1,4-C$_6$H$_4$ | H | 2,4-Dichlorophenyl | 0.93 |
| 24 | CH$_3$ | 1,4-C$_6$H$_4$ | H | 2,6-Dimethyl-5-heptenyl | 1.09 |
| 25 | CH$_3$ | CH=CHCH$_2$O | 3-Br | 4-Bromophenyl | 1.28 |
| 26 | CH$_3$ | 1,4-C$_6$H$_4$ | H | Pentyl | 1.30 |
| 27 | Allyl | 1,4-C$_6$H$_4$ | H | 2,4-Dibromophenyl | 1.45 |
| 28 | Allyl | (CH$_2$)$_5$O | H | 4-Fluorophenyl | 1.50 |
| 29 | Allyl | 1,4-C$_6$H$_4$ | H | 3,4-Dichlorophenyl | 1.60 |
| 30 | CH$_3$ | (CH$_2$)$_5$O | 3-Cl | 4-Bromophenyl | 1.70 |
| 31 | Allyl | (CH$_2$)$_6$ | H | 4-Cyanophenyl | 1.98 |
| 32 | CH$_3$ | 1,4-C$_6$H$_4$ | H | 4-Iodophenyl | 2.30 |
| 33 | Allyl | CH=CHCH$_2$O | 3-Br | 4-Bromophenyl | 2.50 |
| 34 | CH$_3$ | 1,4-C$_6$H$_4$ | H | 3,4-Dichlorophenyl | 2.80 |
| 35 | Allyl | (CH$_2$)$_5$O | 3-Cl | 4-Iodophenyl | 2.90 |
| 36 | CH$_3$ | 1,4-C$_6$H$_4$ | 2-Cl | 4-Bromophenyl | 2.90 |
| 37 | Allyl | (CH$_2$)$_5$O | 3-Br | 4-Bromophenyl | 3.20 |
| 38 | Allyl | (CH$_2$)$_5$O | 3-Cl | 4-Bromophenyl | 3.20 |
| 39 | Allyl | (CH$_2$)$_5$ | H | 4-Bromophenyl | 3.50 |
| 40 | CH$_3$ | CH=CHCH$_2$O | H | 4-Nitrophenyl | 3.50 |
| 41 | CH$_3$ | (CH$_2$)$_5$O | H | 4-Fluorophenyl | 3.60 |
| 42 | C$_2$H$_5$ | 1,4-C$_6$H$_4$ | H | Phenyl | 4.10 |
| 43 | CH$_3$ | (CH$_2$)$_5$O | H | 4-Nitrophenyl | 4.20 |
| 44 | CH$_3$ | (CH$_2$)$_6$ | H | 4-Cyanophenyl | 4.30 |
| 45 | CH$_3$ | (CH$_2$)$_6$ | 2-CH$_3$ | Phenyl | 4.30 |
| 46 | CH$_3$ | 1,4-C$_6$H$_4$ | H | 2-Methylphenyl | 4.30 |
| 47 | CH$_3$ | 1,4-C$_6$H$_4$ | H | Propyl | 4.40 |
| 48 | Allyl | 1,4-C$_6$H$_4$ | H | 4-Fluorophenyl | 4.86 |
| 49 | Allyl | (CH$_2$)$_5$O | 3-Cl | Phenyl | 5.60 |
| 50 | CH$_3$ | 1,4-C$_6$H$_4$ | 2-CH$_3$ | 4-Bromophenyl | 5.60 |
| 51 | Allyl | 1,4-C$_6$H$_4$ | 2-CH$_3$ | Phenyl | 5.80 |
| 52 | CH$_3$ | (CH$_2$)$_6$O | H | Phenyl | 5.90 |
| 53 | CH$_3$ | 1,4-C$_6$H$_4$ | H | 2,4-Difluorophenyl | 6.00 |
| 54 | C$_3$H$_7$ | 1,4-C$_6$H$_4$ | H | Phenyl | 7.20 |
| 55 | CH$_3$ | CH=CHCH$_2$O | 3-Cl | Phenyl | 7.60 |

An $EC_{50}$ value of 4.00 nM/l was determined in the above experiment for 2,4-difluorophenyl 4'-[(allylmethylamino)methyl]-4-biphenylyl ketone hydrochloride.

A procedure analogous to the experiment described in J. Biol. Chem. 256 (1981), 11923–11931 was carried out for the further demonstration of the cholesterol-lowering activity of the compounds of formula I and their salts. Thus, the inhibition of cholesterol :synthesis in human hepatoma cells (Hep G2) was determined on the basis of the stimulation of the LDL receptors induced in parallel. The cells were placed in microtitre plates and treated with the cholesterol synthesis inhibitor. The concentration of the LDL receptor is measured by ELISA methodology, with the C7-LDL antibody being used as the primary antibody. The $EC_{50}$ values in nM/l in Table B hereinafter correspond to the concentration of cholesterol synthesis inhibitor which increases the activity of the receptor by 50% in comparison to the control, that is, untreated cells.

TABLE B

| | Formula I ($R^1$ = methyl) | | | | | $EC_{50}$ |
|---|---|---|---|---|---|---|
| | $R^2$ | L | $R^3$ | Q | n | nm/l |
| Compound No. | | | | | | |
| 1 | Allyl | CH=CHCH$_2$O | H | 4-Bromophenyl | 0 | 50 |
| 2 | Allyl | 1,4-C$_6$H$_4$ | H | 4-Cyanophenyl | 0 | 43 |
| 3 | Allyl | CH=CHCH$_2$O | H | 4-Nitrophenyl | 0 | 63 |
| 4 | CH$_3$ | 1,4-C$_6$H$_4$ | H | 2-Cl-4-NO$_2$-phenyl | 0 | 153 |
| 7 | Allyl | CH=CHCH$_2$O | H | 2,4-(Cl)-phenyl | 0 | 82 |
| Example No. | | | | | | |
| 9a | Allyl | (CH$_2$)$_5$O | H | 4-Bromophenyl | 0 | 51 |
| 9c | Allyl | (CH$_2$)$_5$O | 3-F | 4-Bromophenyl | 0 | 203 |
| 9d | Allyl | (CH$_2$)$_5$O | 2-F | 4-Bromophenyl | 0 | 57 |
| 9f | Allyl | CH=CHCH$_2$O | 3-F | 4-Bromophenyl | 0 | 10 |
| 9g | Allyl | CH=CHCH$_2$O | H | Isohexyl | 0 | 177 |
| 9h | Allyl | CH=CHCH$_2$O | H | 4-Iodphenyl | 0 | 94 |
| 9j | Allyl | CH=CHCH$_2$O | 3-F | 4-Cyanophenyl | 0 | 19 |
| 9l | Allyl | CH=CHCH$_2$O | 3-F | 2,6-(F)$_2$-phenyl | | 220 |
| 9m | Allyl | CH=CHCH$_2$O | H | 4-Methyl-3-pentenyl | 0 | 34 |
| 9n | Allyl | CH=CHCH$_2$O | 2-F | 4-Bromophenyl | 0 | 133 |
| 9p | Allyl | CH=CHCH$_2$O | 3-F | 4-Methyl-3-pentenyl | 1 | 98 |
| 9r | Allyl | CH=CHCH$_2$O | H | 4-Bromophenyl | 1 | 222 |
| 9s | C$_2$H$_5$ | CH=CHCH$_2$O | H | 4-Bromophenyl | 0 | 122 |

The 2- or 3-positions of a substituent $R^3$ in Tables A and B above correspond to the ortho- and, respectively, meta-position to the —(CH$_2$)$_n$C(O)Q group present in formula I.

The toxicity of these compounds is low, for example compound No. 20 has a LD$_{50}$ of 1250–2500 mg/kg per os in the mouse.

The compounds of formula I and their salts can be used as active ingredients in pharmaceutical medicaments. The pharmaceutical preparations are administered orally, for example, in the form of tablets, coated tablets, dragés, hard and soft gelatin capsules, solutions, emulsions or suspensions. The active ingredient can be mixed with pharmaceutically inert, inorganic or organic carriers in order to prepare such medicaments. Lactose, corn starch, talc, stearic acid or its salts can be used, for example, as carriers for tablets, coated tablets, dragés and hard gelatin capsules. Suitable carriers for soft gelatin capsules are, for example, vegetable oils, waxes or fats; depending on the nature of the active ingredient no carriers are, however, usually required in the case of soft gelatin capsules. Suitable carriers for the preparation of solutions and syrups are, for example, water, saccharose, invert sugar and glucose. The pharmaceutical compositions can also contain preservatives, solubilizers, stabilizers, wetting agents, emulsifiers, sweeteners, colorants, flavorants, salts for varying the osmotic pressure, buffers, coating agents or antioxidants. They can also contain other therapeutically active substances.

As mentioned earlier, cholesterol-lowering medicaments which contain a compound of formula I or a pharmaceutically acceptable salt thereof are also an object of the invention, as is a process for the preparation of such medicament, which comprises bringing one or more of the said active ingredients and, if desired, one or more other therapeutically valuable substances into a galenically administratable form. As mentioned earlier, the active ingredients can be used in the control or prevention of illnesses, such as, hypercholesterolemia and atherosclerosis. The dosage can vary within wide limits and will, of course, be fitted to individual requirements in each particular case. In general, a daily dosage of about 2 mg to about 2 g, preferably of about 10 to about 100 rag, can be utilized in the case of oral administration. The daily dosage can be taken in one, two or three single doses, for example, with food.

The preparation of previously undisclosed species of formula 1 is described in the following Examples.

EXAMPLE 1

100 ml of a 10 percent aqueous sodium hydroxide solution are added to a solution of 34.5 g of dibromohexane, 9.9 g of 3-chloro-4-hydroxy-benzophenone and 1.6 g of tetrabutylammonium bromide in 100 ml of methylene chloride. The heterogeneous mixture is stirred at room temperature overnight. The organic phase is separated, dried over sodium sulfate and evaporated. By chromatography of the residue on silica gel with hexane/ethyl acetate 7:3, there is obtained 4-[(6-bromo-hexyl)oxy]-3-chlorobenzophenone, m.p. 58° C.

A solution of 3.0 g of the obtained benzophenone in 30 ml of ethanol is heated to 90° C. in a pressure tube for 1.5 hours with 16 ml of a 33 percent solution of N-allyl-methylamine in ethanol. After cooling, the mixture is poured into water and extracted three times with ethyl acetate. The organic phases, dried over sodium sulfate, are evaporated and the residue is chromatographed on neutral aluminum oxide with hexane/ethyl acetate (7:3), and there is obtained 4-[[6-(allylmethyl-amino)hexyl]oxy]-3-chlorobenzophenone, m.p. of the hydrochloride is 133°C.

EXAMPLE 2

Analogously to Example 1 a) from 3,4'-dibromo-4-hydroxybenzophenone, there is obtained, via 4-[(6-bromohexyl)oxy]-3,4'-dibromobenzophenone, m.p. 97° C., 4-[[6-(allylmethylamino)hexyl]oxy]-3,4'-dibromobenzophenone, m.p. of the hydrochloride is 126°–127° C., b) from 3,4'-dibromo-4-hydroxybenzophenone and trans 1,4-dibromobutene, there is obtained, via 4-[(4-bromo-2-butenyl)oxy]-3,4'-dibromobenzophenone. 4-[[4-(allylmethyl-amino)-2-butenyl]oxy]-3,4'-dibromobenzophenone, m.p. of the hydrochloride is 115°–116° C., c) from 3-chloro-4'-iodo-4-hydroxybenzophenone and 1,6-dibromohexane, there is obtained, via 3-chloro-4'-iodo-4-[(6-bromohexyl)oxy]benzophenone, 3-chloro-4'-iodo-4-[[6-(ally-methylamino)hexyl]oxy]benzophenone, which is converted into the hydrochloride, MS: m/e 511 (M$^+$, 2.4%). 484 (2%), 482 (4%), 231 (2.5%) 154 (3.3%), 84 (100%), d) via 4'-bromo-3-chloro-4-[(6-bromohexyl)oxy]benzophenone (Example 3c), there is obtained 4'-bromo-3-chloro-4-[[6-(allyl-methylamino)hexyl]oxy]benzophenone, which is converted into the hydrochloride, MS: m/e 465 (M$^+$, 2%). 463 (1.5%), 436 (4%), 434 (3%), 155 (3%), 154 (4%), 84 (100%).

EXAMPLE 3

Analogously to Example 1 a) via 4-[(4-bromo-2-butenyl)oxy]-3,4'-dibromobenzophenone (Example 2b) using dimethylamine in place of N-allyl-methylamine, there is obtained 2,4-[[(4-dimethylamino)-2-butenyl]oxy]-3,4'-dibromobenzophenone, which is converted into the hydrochloride, m.p. 166°–167° C., b) from 3-chloro-4-hydroxybenzophenone and 1,4-dibromobutene, there is obtained, via 4-[(4-bromo-2-butenyl)oxy]-3-chlorobenzo-phenone, m.p. 96°–97° C., 4-[[4-(dimethylamino)-2-butenyl]oxy]-3-chlorobenzophenone, which is converted into the hydrochloride, m.p. 195° C., c) from 4'-bromo-3-chloro-4-hydroxybenzophenone and 1,6-dibromohexane, there is obtained, via 4'-bromo-3-chloro-4-[(6-bromohexyl)oxy]benzophenone, 4'-bromo-3-chloro-4-[[6-(dimethyl-amino)hexyl]oxy]benzophenone, which is converted into the hydrochloride, MS: m/e 402 (M$^+$-Cl, 0.2%), 185 (1.3%), 183 (1.6%), 155 (2%), 128 (4%), 58 (100%).

EXAMPLE 4 a)

35 ml of nitrobenzene are cooled in an ice-bath and then treated in succession with 5.2 g of aluminum chloride and 5.0 g of 4-methyl-biphenyl. The mixture is brought to room temperature and then treated with 7.7 g of 3,4-dichlorobenzyl chloride. The mixture is stirred at room temperature, poured into water and extracted with methylene chloride. The extracts are washed with 2N hydrochloric acid and water, dried over magnesium sulfate and evaporated. The residue is chromatographed on silica gel with toluene/ethyl acetate 9:1. 3,4Dichlorophenyl 4'-methyl-4-biphenylyl ketone is obtained.

b)

A mixture of 5.0 g of 3,4-dichlorophenyl 4'-methyl-4-biphenylyl ketone, 2.7 g of N-bromosuccinimide and 20 mg of azaisobutyronitrile in 70 ml of carbon tetrachloride is heated to boiling under reflux. The precipitated material is filtered and the filtrate is evaporated. The residue is recrystallized from toluene/cyclohexane. 3,4-Dichlorophenyl 4'-bromomethyl-4-biphenylyl ketone is obtained.

c)

1.0 g of 3,4-dichlorophenyl 4'-bromomethyl-4-biphenylyl ketone and 20 ml of a 33 percent solution of dimethylamine in ethanol are heated to boiling for 4 hours, whereupon the mixture is evaporated. The residue is taken up in ether and treated with an ethereal hydrogen chloride solution. The precipitated hydrochloride is filtered and dried. 3,4-Dichlorophenyl 4'-[(dimethylamino)methyl]-4-biphenylyl ketone hydrochloride, m.p. 223°C., is obtained.

EXAMPLE 5

1.0 g of 3,4-dichlorophenyl 4'-bromomethyl-4-biphenylyl ketone, 1.5 ml of N-allylmethylamine and 0.84 g of potassium carbonate in 25 ml of ethanol are heated to boiling under reflux for 4 hours. The mixture is evaporated and the residue is extracted with ether. The extracts are dried over magnesium sulfate and treated with an ethereal hydrogen chloride solution. The precipitated hydrochloride is filtered and dried. 4'[(Allylmethylamino)methyl]-4-biphenylyl 3,4-dichlorphenyl ketone hydrochloride, m.p. 160° C., is obtained.

EXAMPLE 6 a)

A solution of the Grignard reagent prepared from 344 mg of magnesium and 2.27 g of 1,4-dibromobenzene in 15 ml of THF (tetrahydrofuran) is added dropwise to a suspension of 2 g of 4-bromo-N,N-dimethylbenzylamine and 158 mg of tetrakistriphenylphosphinepalladium in 10 ml of THF. The addition is carried out at room temperature and under an argon atmosphere. After completion of the addition, the mixture is heated to boiling for an additional 5 hours and then evaporated under reduced pressure. The residue is then treated with ether and saturated ammonium chloride solution and the aqueous phase is separated. This is extracted with ether. The organic extracts are washed with saturated sodium chloride solution, dried over magnesium sulfate and evaporated. The residue is purified by chromatography on silica gel while eluting with methylene chloride/methanol 9:1. 4'-Bromo-N,N-dimethylbiphenylmethanamine, m.p. 60°–62°C., is obtained.

b)

A solution of the Grignard reagent prepared from 0.94 g of 4'-bromo-N,N-dimethylbiphenylmethanamine and 146 mg of magnesium in 5 ml of THF is added dropwise to a solution of 1.07 g of citronellal in 10 ml of THF. The addition is carried out at room temperature and under an argon atmosphere. The mixture is then stirred at room temperature for 6 hours and subsequently hydrolyzed with 50 ml of saturated ammonium chloride solution. The mixture is extracted with ether, the extracts are dried over magnesium sulfate and evaporated. After chromatography on silica gel with methylene chloride/methanol 9:1 as the eluent, there is obtained (RS)-4'-[(dimethylaminomethyl)-4-biphenylyl]-α-(2,6-dimethyl-5-heptenyl)methanol, MS m/e: M$^+$365 (21%), 321 (19%), 280 (36%), 58 (100%).

c)

A solution of 406 mg of DMSO (dimethylsulfoxide) in 2 ml of methylene chloride is added to a solution of 327 mg oxalyl chloride in 10 ml of methylene chloride at −70°C. The reaction mixture is stirred for 2 minutes, whereupon a solution of 810 mg of the product from Step b) in 5 ml of methylene chloride is added thereto. The reaction mixture is stirred for an additional 15 minutes and then treated at −70°C. with 1.18 g of triethylamine. The reaction mixture is then left to warm to room temperature and is treated with an aqueous sodium carbonate solution. The aqueous phase is extracted with methylene chloride. The organic phases are combined, washed with saturated sodium chloride solution and dried over magnesium sulfate. A hot solution of 263 mg of fumaric acid in 5 ml of ethanol is added to the material obtained after concentration and evaporation. The precipitated fumarate is recrystallized from ethanol. (RS)-4'-(Dimethylaminomethyl)-4-biphenyl 2,6-dimethyl-5-heptenyl ketone fumarate, m.p. 116°–123°C., is obtained.

EXAMPLE 7 a)

3-Chloro-4'-methylbiphenyl, b.p. 110°–115°C./20 Pa, is obtained from 4-bromotoluene and 3-chlorobromobenzene analogously to Example 6 a).

b)

A mixture of 4.76 g of 3-chloro-4'-methylbiphenyl, 2.94 g of hexamethylenetetramine and 30 ml of trifluoroacetic acid is heated to boiling under reflux for 5 days. The reaction mixture is then concentrated and treated with ice-water, whereupon it is stirred for 15 minutes, made basic with sodium carbonate and extracted with ether. After evaporation of the ethereal extracts and chromatography of the residue on silica gel with methylene chloride/methanol 9:1 as the eluent, there is obtained 2-chloro-4-(4'-methylphenyl-)benzaldehyde, b.p. 210°–215°C./25 Pa.

c)

Analogously to Example 6 $b$) and 6 $c$), from 2-chloro-4-(4'-methylphenyl)benzaldehyde and 1,4-dibromobenzene, there is obtained p-bromophenyl 2-chloro-4'-methyl-4-biphenyl ketone as a colorless oil, MS m/e: 386 ($M^+$, 46%), 306 (9%), 229 (100%).

d)

Analogously to Example 4 b), from p-bromophenyl 2-chloro-4'-methyl-4-biphenyl ketone, there is obtained 4'-bromomethyl-2-chloro-p-bromophenyl-4-biphenyl ketone.

e)

Analogously to Example 4c), by treating 4'-bromomethyl-2-chloro-p-bromophenyl-4-biphenyl ketone with dimethylamine and then with hydrogen chloride, there is obtained p-bromophenyl-2-chloro-4'-[(dimethylamino)methyl]-4-biphenylyl ketone hydrochloride, m.p. 189°–191° C.

EXAMPLE 8

A solution of the Grignard reagent prepared from 228 mg of magnesium and 1.42 g of n-propyl bromide in 10 ml of THF is added dropwise under argon at 0 C. to a solution of 1.16 g of 4'-[(dimethyl-amino)methyl]-N-methoxy-N-methyl-4-biphenylcarboxamide in 10 ml of THF. After completion of the addition, the mixture is stirred at room temperature for an additional 5 hours and then evaporated under reduced pressure. The residue is treated with methylene chloride and saturated ammonium chloride solution and the aqueous phase is separated. This is extracted with methylene chloride. The organic extracts are washed with saturated sodium chloride solution, dried over magnesium sulfate and evaporated. The residue is purified by chromatography on silica gel while eluting with methylene chloride-methanol 95:5. 4'-[(Dimethyl-amino)methyl-4-biphenylyl propyl ketone fumarate, m.p. 155°–156°C., is obtained after reaction with fumaric acid in ethanol.

EXAMPLE 9

STARTING MATERIALS

A)

A mixture of 41 g of 4-hydroxybenzoic acid and 400 ml of hexamethyldisilazane is heated at reflux for 2 hours, then cooled, concentrated and dissolved in 400 ml of methylene chloride. After the addition of 3 drops of DMF, 28 ml of oxalyl chloride are added dropwise. The mixture is stirred, then concentrated and dried. The acid chloride is suspended in 520 ml of methylene chloride with 31 g of N,O-dimethylhydroxylamine hydrochloride and the mixture is treated at 0 C. for 2 hours with 73 ml of N-methylmorpholine. The mixture is warmed up overnight, taken up in ethyl acetate and washed with water, 10% aqueous $KHSO_4$ solution and saturated aqueous. $NaHCO_3$ solution. The organic phase is dried, filtered and evaporated. There are obtained 76 g of N-methoxy-N-methyl-trimethylsilanyloxy-benzamide, MS: m/e 238 ($M^{30}$ —$CH_3$).

B)

Analogous to paragraph A),

Ba) from 4-hydroxyphenylacetic acid, there is obtained N-methoxy-N-methyl-2-(4-trimethylsilanyloxy-phenyl)-acetamide, MS: m/e 267 ($M^+$), 252 ($M^{30}$ —$CH_3$), Bb) from 3-fluoro-4-hydroxy-phenylacetic acid, there is obtained N-methoxy-N-methyl-2-(3-fluoro-4-trimethylsilanyloxy-phenyl)-acetamide, MS: m/e 285 ($M^+$).

C)

A solution of 6.3 g of N-methoxy-N-methyl-trimethylsilanyloxybenzamide is added dropwise at 0° C. to a Grignard reagent prepared from 1 g of magnesium and 5.7 g of 1-bromo-4-methyl-3-pentene. The 15 reaction mixture is left to stand at room temperature overnight while stirring. The mixture is treated with 10% aqueous $KHSO_4$ solution and then extracted with ethyl acetate. The organic phase is washed neutral with 10% aqueous NaCl solution, then dried and concentrated. The silyl group is cleaved in 10% aqueous THF with 1N hydrochloric acid. Then, the product is taken up in methylene chloride, dried and evaporated. After chromatography over silica gel while eluting with methylene chloride/5% methanol, there are obtained 2.1 g of 1-(4-hydroxy- phenyl)-5-methyl-hex-4-en-1-one. MS: m/e 204 ($M^+$).

D)

Analogously to paragraph C), from N-methoxy-N-methyl-2-(3-fluoro-4-trimethylsilanyloxy-phenyl)-acetamide (paragraph Bb), there is obtained 1-(3-fluoro-4-hydroxyphenyl)-6-methyl-hept-5-en-2-one, MS: m/e 236 ($M^+$).

E)

A solution of 45 ml of n-butyllithium (1.6M in hexane) is added dropwise to a suspension, cooled to -78 C., of 18.2 g of 1,4-dibromobenzene in 140 ml of THF. Then, 10 g of N-methoxy-N-methyl-2-(3-fluoro-4-trimethylsilanyloxyphenyl)-acetamide (paragraph. Bb)) in 35 ml of THF are added dropwise at −78° C. The reaction mixture is stirred at −78 C. for 2 hours, then left to stand at room temperature for 1 hour while stirring. After dilution with ethyl acetate, the mixture is washed with 10% aqueous $KHSO_4$ solution, saturated $NaHCO_3$ solution and 10% aqueous NaCl solution. After extraction with ethyl acetate, the organic phases are dried and concentrated. Then, the silyl group is cleaved with 105 ml of THF, 11 ml of $H_2O$ and 5 drops of 1N HCl. Concentration, dissolution in methylene chloride, drying and column chromatography over silica gel with methylene chloride/0.5% methanol as the eluent, give 9.2 g of 1-(4- bromo-phenyl)-2-(3-fluoro-4-hydroxy-phenyl)-ethanone. MS: m/e 308 (M$^+$,1 Br).

F)

Analogously to paragraph E), from N-methoxy-N-methyl-2-(4-trimethylsilanyloxy-phenyl)-acetamide (paragraph Ba)), there is obtained 1-(4-bromo-phenyl)-2-(4-hydroxy-phenyl)-ethanone, MS: m/e 290 (M$^+$, 1 Br).

G)

14 ml of nitrobenzene are cooled in an ice-bath and then mixed in succession with 3.8 g of AlCl$_3$ and 3.7 g of 5-methyl-hexanoyl chloride in 5 mi of nitrobenzene. The mixture is stirred and then treated with 2.7 ml of 2-fluoroanisole. The solution is stirred overnight, then poured into ice-water and extracted with methylene chloride. The extracts are washed with water and 10% aqueous NaCl solution, and thereafter dried and concentrated and recrystallized using pentane. 5.31 g of 1-(3-fluoro-4-methoxyphenyl)-5-methyl-hexan-1-one, MS: m/e 238 (M$^+$), are obtained.

H)

Analogously to paragraph G)

Ha) from 4-bromo-benzoyl chloride and 2-fluoro-anisole, there is obtained (4-bromo-phenyl)-(3-fluoro-4-methoxyphenyl)-methanone, m.p. 142°–143° C., Hb) from 4-cyano-benzoyl chloride and 2-fluoro-anisole, there is obtained 4-(3-fluoro-4-methoxy-benzoyl)-benzonitrile, m.p. 132.5°–133° C., Hc) from 4-bromo-benzoyl chloride and 3-fluoro-anisole, there is obtained (4-bromo-phenyl)-(2-fluoro-4-methoxyphenyl)-methanone, MS: m/e 308 (M$^+$, 1 Br), Hd) from 2,6-difluoro-benzoyl chloride and 2-fluoro-anisole, there is obtained (2,6-difluoro-phenyl)-(3-fluoro-4-methoxy-phenyl)-methanone, m.p. 79°–83° C.

I)

A solution of 3.9g of (2,6-difluoro-phenyl)-(3-fluoro-4-methoxy-phenyl)-methanone (paragraph Hd)) in 30 ml of acetic acid is stirred with 20 ml of aqueous 62% HBr solution at 125° C., then evaporated, re-evaporated with toluene and taken up in ethyl acetate. The organic phase is washed with sat. aqueous NaHCO$_3$ solution and 10% NaCl solution and then dried. 3.6g of (2,6-difluoro-phenyl)-(3-fluoro-4-hydroxy-phenyl)-methanone MS: m/e 252 (M$^+$), are obtained.

J)

Analogously to paragraph (I)

Ja) from (4-bromo-Phenyl)-(3-fluoro-4-methoxy-phenyl)-methanone (paragraph Ha)), there is obtained (4-bromo-phenyl)-(3-fluoro-4-hydroxy-phenyl)-methanone, m.p. 183°–184° C., Jb) from (4-bromo-phenyl)-(2-fluoro-4-methoxy-phenyl)-methanone (paragraph Hc), there is obtained (4-bromo-phenyl)-(2-fluoro-.4-hydroxy-phenyl)-methanone, MS: m/e 294 (M$^+$, 1 Br), Jc) from anisole and 5-methyl-hexanoyl chloride, there is directly obtained, via 1-(4-methoxy-phenyl)-5-methyl-hexan-1-one, 1-(4-hydroxy-phenyl)-5-methyl-hexan-1-one, MS: m/e 206 (M$^+$).

K)

A solution of 50g of 4-(3-fluoro-4-methoxy-benzoyl)benzonitrile in 550 ml of methylene chloride is treated with 70 ml of BBr$_3$ at 5° C. and stirred at room temperature. 1l of 1M NaOH is added dropwise while cooling with ice. Then, the mixture is extracted with saturated aqueous NH$_4$Cl solution and methylene chloride. The organic phase is washed with water and dried. After recrystallization from ether, there are obtained 34 g of 4-(3-fluoro-4-hydroxybenzoyl)-benzonitrile, m.p. 168.5°–169.5° C.

Products

Analogously to Example 1 a) from 4'-bromo-4-hydroxybenzophenone and 1,6-dibromohexane, there is obtained, via 4'-bromo-4-[(6-bromohexyl)oxy]benzophenone and reaction with N-allyl-methylamine, [4-[6-(allyl-methyl-amino)-hexyloxy]-phenyl]-(4-bromo-phenyl)-methanone hydrobromide, m.p. 117°–119° C., b) from 4'-bromo-4-hydroxybenzophenone and 1,4-dibromobutane, there is obtained, via 4'-bromo-4-[(6-bromobutyl)oxy]benzophenone and reaction with N-allyl-methylamine, [4-[4-(allyl-methyl-amino)-butoxy]-phenyl]-(4-bromo-phenyl)-methanone hydrobromide, m.p. 149°–151° C., c) from (4-bromo-phenyl)-(3-fluoro-4-hydroxy-phenyl)-methanone (paragraph Ja) and 1,6-dibromohexane, there is obtained, via [4-(6-bromo-hexyl)-3-fluoro-phenyl]-(4-bromo-phenyl)-methanone and reaction with N-allyl-methylamine, [4-[6-(allyl-methyl-amino)-hexyloxy]-2-fluoro-phenyl]-(4-bromo-phenyl)-methanone which is converted into the hydrochloride, MS: m/e 447 (M$^+$, 1 Br), d) from (4-bromo-phenyl)-(2-fluoro-4-hydroxy-phenyl)-methanone (paragraph Jb) and 1,6-dibromohexane; there is obtained, via [4-(6o bromo-hexyl)-2-fluoro-phenyl]-(4-bromo-phenyl)-methanone and reaction with N-allyl-methylamine, [4-[6-(allyl-methyl-amino)-hexyloxy]-2-fluoro-phenyl]-(4-bromo-phenyl)-methanone, which is convened into the hydrochloride, m.p. 106°–109° C., e) from 4'-trifluoromethyl-4-hydroxybenzophenone and (E)-1,4-dibromobutene, there is obtained, via (E)-[4-[4-bromo-but-2-enyloxy]Phenyl]-(4-trifluoromethyl-phenyl)-methanone and reaction with N-allyl-methylamine, (E)-[4-[4-(allyl-methyl-amino)-but-2-enyloxy]phenyl]-(4-trifluoromethyl-phenyl)-methanone, which is converted into the hydrochloride, MS: m/e M 390 (M+H$^+$), f) from (4-bromo-phenyl)-(3-fluoro-4-hydroxy-phenyl)-methanone (paragraph Ja) and (E)-1,4-dibromobutene, there is obtained, via (E)-[4-(4-bromo-but-2-enyloxy)-3-fluoro-phenyl]-(4-bromo-phenyl)-methanone and reaction with N-allyl-methylamine, (E)-[4-[4-(allyl-methyl-amino)-but-2-enyloxy]-3-fluoro-phenyl]-(4-bromo-phenyl)-methanone, which is converted into the hydrochloride, MS: m/e 418 (M+H$^+$, 1 Br), g) from 1-(4-hydroxy-phenyl)-5-methyl-hexan-1-one (paragraph Jc) and (E)-1,4-dibromobutene, there is obtained, via (E)-1-[4-[4.-bromobut-2-enyloxy]-phenyl]-5-methyl-hexan-1-one and reaction with N-allyl-methylamine, (E)-I -[4-[4-(allyl-methyl-amino)-but-2-enyloxy]-phenyl]-5-methyl-hexan-1-one, which is converted into the hydrochloride, m.p. 105°–106° C., h) from (4-hydroxy-phenyl)-(4-iodo-phenyl)-methanone and (E)-I,4-dibromobutene, there is obtained, via (E)-[4-[4-bromo-but-2-enyloxy]-phenyl]-(4-iodo-phenyl)-methanone and reaction with N-allyl-methylamine, (E)-[4-[4-(allyl-methyl-amino)-but-2-enyloxy]-phenyl]-(4-iodo-phenyl)-methanone, which is converted into the hydrochloride, m.p. 152°–153° C.

i) from 1-(3-fluoro-4-methoxy-phenyl)-5-methyl-hexan-1-one (paragraph G), there is obtained, via 1-(3-fluoro-4-hydroxy-phenyl)-5-methyl-hexan-1-one and (E)-I -[4-bromo-but-2-enyloxy]- 3-fluoro-phenyl]-5-methyl-hexan-1-one and reaction with N-allyl-methylamine, (E)-1-[4-(ally-methyl-amino)-but-2-enyloxy]-3-fluoro-phenyl]-5-methyl-hexan-1-one, which is isolated as the hydrobromide, m.p. 106°–107° C., j) from 4-(3-fluoro-4-hydroxy-benzoyl)-benzonitrile (paragraph K) with (E)-1,4-dibromobutene, there is obtained, via (E)-4-[4-(4-bromo-but-2-enyloxy)-3-fluoro-benzoyl]-benzonitrile and reaction with N-allyl-methylamine, (E)-[4-[4-(allyl-methyl-amino)-but-2-enyloxy]-3-fluoro-benzoyl]-benzonitrile, MS: m/e 364 ($M^+$), k) from 4-(4-hydroxy-benzoyl)-benzonitrile with (E)-1,4-dibromobutene, there is obtained, via (E)-4-[4-(4-bromo-but-2-enyloxy)-benzoyl]-benzonitrile and reaction with N-allyl-methylamine, (E)-4-[4-[4-(allyl-methyl-amino)-but-2-enyloxy]-benzoyl]-benzonitrile, MS: m/e 346 ($M^+$), l) from (2,6-difluoro-phenyl)-(3-fluoro-4-hydroxy-phenyl)-methanone (paragraph I) and (E)-1,4-dibromobutene, there is obtained, via (E)-[4-[4-bromo-but-2-enyloxy]-3-fluoro-phenyl]-(2,6-difluoro-phenyl)-methanone and reaction with N-allyl-methylamine, (E)-[4-[4-(allyl-methyl-amino)-but-2-enyloxy]-3-fluoro-phenyl]-(2,6-difluoro-phenyl)-methanone which is isolated as the hydrobromide, m.p. 162° C., m) from 1-(4-hydroxy-phenyl)-5-methyl-hex-4-en-1-one (paragraph C) and (E)-1,4-dibromobutene, there is obtained, via (E)-1-[4-[4-bromo-but-2-enyloxy]-phenyl]-5-methyl-hex-4-en-1-one and reaction with N-allyl-methylamine, (E)-I -[4-[4-(allyl-methyl-amino)-but-2-enyloxy]phenyl]-5-methyl-hex-4-en-1-one, which is isolated as the fumarate, MS: m/e 327 ($M^+$), n) from (4-bromo-phenyl)-(2-fluoro-4-hydroxy-phenyl)-methanone (paragraph Jb) and (E)-1,4-dibromobutene, there is obtained, via (E)-[4-[4-bromo-but-2-enyloxy]-2-fluoro-phenyl]-(4-bromo-phenyl)-methanone and reaction with N-allyl-methyl-amine, (E)-[4-[4-(allyl-methyl-amino)-but-2-enyloxy]-2-fluoro-phenyl]-(4-bromo-phenyl)-methanone, which is isolated as the hydrochloride, m.p. 88–92 C., o) from 4-fluoro-4'-hydroxy-benzophenone and (E)-1,4-dibromobutene, there is obtained, via (E)-[4-[4-bromo-but-2-enyloxy]-phenyl]-(4-fluoro-phenyl)-methanone and reaction with N-allyl-methylamine, (E)-[4-[4-(allyl-methyl-amino)-but-2-enyloxy]-phenyl]-(4-fluoro-phenyl)-methanone, which is isolated as the hydrochloride, MS: m/e 338 (M–$H^+$), p) from 1-(3-fluoro-4-hydroxy-phenyl)-6-methyl-hept-5-en-2-one (paragraph D) and (E)-1,4-dibromobutene, there is obtained, via (E)-1-[4-[4-bromo-but-2-enyloxy]-3-fluoro-phenyl]-6-methyl-hept-5-en-2-one and reaction with N-allyl-methylamine, (E)-1-[4-[4-(allyl-methylamino)-but-2-enyloxy]-3-fluoro-phenyl]-6-methyl-hept-5-en-2-one, which is isolated as the fumarate, MS: m/e 359 ($M^+$), q) from 1-(4-bromo-phenyl)-2-(3-fluoro-4-hydroxy-phenyl)-ethanone (paragraph E) and (E)-1,4-dibromobutene, there is obtained, via (E)-2-[4-[4-bromo-but-2-enyloxy]-3-fluoro-phenyl]-(4-bromo-phenyl)-ethanone and reaction with N-allyl-methylamine, (E)-2-[4-[4-(allyl-methylamino)-but-2-enyloxy]-3-fluoro-phenyl]-(4-bromo-phenyl)-ethanone, which is isolated as the hydrochloride, m.p. 114°–116° C., r) from 1-(4-bromo-phenyl)-2-(4-hydroxy-phenyl)-ethanone (paragraph Fa) and (E)-1,4-dibromobutene, there is obtained, via (E)-2-[4-(4-bromo-but-2-enyloxy)-phenyl]-1-(4-bromo-phenyl)-ethanone and reaction with N-allyl-methylamine, (E)-2-[4-[4-(allyl-methyl-amino)-but-2-enyloxy)-phenyl]-1-(4-bromo-phenyl)-ethanone, which is isolated as the hydrochloride, m.p. 150°–153° C., ps) from 4'-bromo-4-hydroxybenzophenone and (E)-1,4-dibromobutene, there is obtained, via (E)-[4-(4-bromo-but-2-enyloxy)-phenyl]-(4-bromo-phenyl)-methanone and reaction with N-ethyl-methylamine, (E)-(4-bromo-phenyl)-[4-[4-(ethyl-methyl-amino)-but-2-enyloxy]-phenyl]-methanone hydrobromide, m.p. 171.5° C. (decomposition).

EXAMPLE 10

Analogously to Example 4c), by treating 4'-bromomethyl-2-chloro-p-bromophenyl 4-biphenyl ketone with N-allyl-methylamine, there is obtained 4'-[(allylmethylamino)methyl]-2-chloro-4-biphenylyl p-bromophenyl ketone, MS: m/e 453 ($M^+$, 1 Br).

EXAMPLE 11

Analogously to Example 8, from 5-bromo-2-methyl-pentene and 4'-[(N-allylmethylamino)methyl]-N-methyl-4-biphenylcarboxamide, there is obtained 4'-[(allylmethylamino)methyl]-4-biphenyl 4-methyl-3-pentenyl ketone, MS: m/e 347 ($M^+$).

Galenical Example

A hard gelatin capsule contains e.g. 3, 125, 6.25, 12.5, 25 or 50 mg of a compound of formula I or a salt thereof and finely crystalline lactose to a final fill weight of 580–590 mg.

We claim:

1. A method of lowering cholesterol which comprises administering to a host requiring such treatment an effective amount of

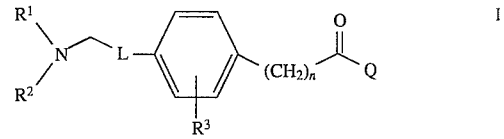

wherein
one of $R^1$ and $R^2$ is $C_{1-7}$-alkyl and the other is $C_{1-7}$-alkyl or $C_{2-6}$-alkenyl-methyl;
L is $C_{1-11}$-alkylene or $C_{2-11}$-alkenylene optionally bonded to the phenyl group via an O atom or L is 1,4-phenylene;
n is 0 or, when L contains an O atom, n is 0 or 1;
Q is $C_{1-7}$-alkyl, $C_{2-10}$-alkenyl or a group of formula

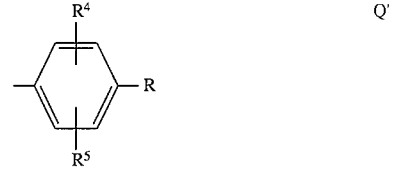

wherein R is H, halogen, $CF_3$, CN or $NO_2$;
$R^3$ and $R^4$ are H, $C_{1-4}$-alkyl or halogen; and
$R^5$ is H or, when R is H, $R^5$ is H or halogen;
or a pharmaceutically acceptable acid addition salt thereof.

2. A method according to claim 1, wherein n is 0 and $R^5$ is H.

3. A method according to claim 1, wherein $R^1$ is methyl and $R^2$ is methyl, ethyl, propyl or allyl.

4. A method according to claim 3, wherein L is the group —CH=CHCH$_2$O—, the trans form of —CH=CHCH$_2$O—, —(CH$_2$)$_5$-, —(CH$_2$)$_6$-, —(CH$_2$)$_3$O— propyl, pentyl, isohexyl, 4-methyl-3-pentenyl or 2,6-dimethyl-5-heptenyl.

5. A method according to claim 4, wherein $R^3$ is H, Br, Cl, F or CH$_3$.

6. A method according to claim 5, wherein Q is propyl, pentyl, isohexyl, 4-methyl-3-pentenyl or 2,6-dimethyl-5-heptenyl.

7. A method according to claim 6, wherein Q is Q' wherein R is H, Br, Cl, F, I, $CF_3$, CN or $NO_2$; $R^4$ is H, Br, Cl, F or CH$_3$; and $R^5$ is H or F.

8. A method according to claim 1 wherein L is $C_{5-11}$-alkylene or $C_{5-11}$-alkyleneoxy, $C_{3-11}$-alkenyloxy, or 1,4-phenylene.

9. A method according to claim 2, wherein L is $C_{5-11}$-alkylene or $C_{5-11}$alkyleneoxy, $C_{3-11}$alkenyloxy, or 1,4phenylene.

10. A method according to claim 9, wherein $R^3$ is H or halogen.

11. A method according to claim 10, wherein Q is $C_{2-10}$-alkenyl, or Q' wherein R is CN, $NO_2$ or halogen, and $R^4$ is H or Cl.

12. A method according to claim 9, wherein $R^1$ is methyl and $R^2$ is methyl or allyl, L is —$(CH_2)_5O$—, —CH=CHCH$_2$O— or 1,4-phenylene, $R^3$ is H or F, and Q is 4-methyl-3-pentenyl or Q' wherein R is Br, Cl, CN or $NO_2$, $R^4$ is H or Cl and $R^5$ is H.

13. A method in accordance with claim 1, wherein the compound of formula I is selected from the group consisting of:

trans-4-[[4-( Allylmethylamino)-2-butenyl]oxy]-4'-bromo-benzophenone;

trans-4-[[4-(allymethylamino)-2-butenyl]oxy]-4'-nitro-benzophenone;

p-[[4'-[(allylmethylamino)methyl]-4-biphenylyl]carbonyl]-benzonitrile;

2-chloro-4-nitrophenyl 4'-[(dimethylamino)methyl]-4-biphenylyl ketone; and trans-4-[[4-(allymethylamino)-2-butenyl]oxy]-2',4'-dichlorobenzophenone.

14. A method in accordance with claim 1, wherein the compound of formula I is selected from the group consisting of:

[4-[6-( Allyl-methyl-amino)-hexyloxy]-phenyl]-(4-bromo-phenyl)-methanone;

[4-[6-(ally-methyl-amino)-hexyloxy]-3-fluoro-phenyl]-(4-bromo-phenyl)-methanone;

[4-[6-(ally-methyl-amino)-hexyloxy]-2-fluoro-phenyl]-(4-bromo-phenyl)-methanone;

(E)-[4-[4-(ally-methyl-amino)-but-2-enyloxy]-3-fluoro-phenyl]-(4-bromo-phenyl)-methanone;

(E)-I -[4-[4-(allyl-methyl-amino)-but-2-enyloxy]-phenyl]-5-methyl-hex-4-en-1-one; and (E)-[4-[4-(ally-methyl-amino)-but-2-enyloxy]-2-fluoro-phenyl]-(4-bromo-phenyl)-methanone.

* * * * *

UNITED STATES PATENT AND TRADEMARK OFFICE
CERTIFICATE OF CORRECTION

PATENT NO. : 5,574,071
DATED : November 12, 1996
INVENTOR(S) : Johannes Aebi, Philipe Guerry, Synése Joliden, Oliver Morand It is certified that error appears in the above-identified patent and that said Letters Patent is hereby corrected as shown below:

In claim 4, column 16, lines 58-59, delete "propyl, pentyl, isohexyl, 4-methyl-3-pentenyl or 2,6-dimethyl-5-heptenyl" and insert -- $(CH_2)_5O$-, -$(CH_2)_6O$- or 1,4-phenylene --.

In claim 8, column 17, line 2, replace "alkenyloxy" with -- alkenylenoxy --.

In claim 9, column 17, line 5, replace "alkenyloxy" with -- alkenylenoxy --.

In claim 14, column 18, line 20, change "I" to --1--.

Signed and Sealed this

Eighth Day of July, 1997

*Attest:*

BRUCE LEHMAN

*Attesting Officer*     Commissioner of Patents and Trademarks